(12) United States Patent
Burroughs, III (10) Patent No.: US 8,894,672 B2
(45) Date of Patent: Nov. 25, 2014

(54) QUADRICEPS TENDON STRIPPER

(76) Inventor: Paul Leach Burroughs, III, Raleigh, NC (US)

( * ) Notice: Subject to any disclaimer, the term of this patent is extended or adjusted under 35 U.S.C. 154(b) by 547 days.

(21) Appl. No.: 13/102,562

(22) Filed: May 6, 2011

(65) Prior Publication Data

US 2012/0283793 A1 Nov. 8, 2012

(51) Int. Cl.
*A61B 17/32* (2006.01)
*A61B 17/17* (2006.01)
*A61B 17/00* (2006.01)
*A61B 18/08* (2006.01)
*A61B 17/16* (2006.01)

(52) U.S. Cl.
CPC ..... *A61B 17/320016* (2013.01); *A61B 17/1767* (2013.01); *A61B 18/082* (2013.01); *A61B 17/1635* (2013.01); *A61B 2017/32004* (2013.01); *A61B 17/1677* (2013.01); *A61B 17/00008* (2013.01); *A61B 17/1604* (2013.01)
USPC .............................. 606/167; 606/171; 30/172

(58) Field of Classification Search
USPC ............. 30/167, 167.1–167.2, 168, 280, 283, 30/287, 299, 301–303, 314, 320; 606/79, 606/82–85, 86 R, 167, 170–172, 184–185, 606/177
See application file for complete search history.

(56) References Cited

U.S. PATENT DOCUMENTS

| | | | |
|---|---|---|---|
| 622,461 A * | 4/1899 | Glardon-Jacquet et al. .... | 142/56 |
| 3,583,390 A | 6/1971 | Jascalevich | |
| 3,844,272 A | 10/1974 | Banko | |
| 4,832,045 A | 5/1989 | Goldberger | |
| 4,985,031 A * | 1/1991 | Buss et al. ...................... | 606/82 |
| 5,391,169 A | 2/1995 | McGuire | |
| 5,570,700 A | 11/1996 | Vogeler | |
| 5,722,977 A * | 3/1998 | Wilhelmy ....................... | 606/84 |
| 5,933,968 A * | 8/1999 | Solomon ......................... | 30/358 |
| 6,035,536 A | 3/2000 | Dewberry | |
| 6,053,928 A | 4/2000 | Van Wyk et al. | |
| 6,258,094 B1 * | 7/2001 | Nicholson et al. .............. | 606/84 |
| 6,391,031 B1 * | 5/2002 | Toomey ........................... | 606/87 |
| 7,285,122 B2 | 10/2007 | Sanford et al. | |
| 8,551,101 B2 * | 10/2013 | Kuczynski ...................... | 606/88 |
| 2005/0149092 A1 | 7/2005 | Dunn | |
| 2006/0212057 A1 | 9/2006 | Djordjevic et al. | |
| 2008/0065113 A1 | 3/2008 | Smith | |
| 2008/0161810 A1 * | 7/2008 | Melkent .......................... | 606/79 |
| 2009/0048485 A1 | 2/2009 | Heisler | |
| 2010/0069944 A1 | 3/2010 | Murakami et al. | |
| 2011/0004214 A1 * | 1/2011 | Skaggs ............................ | 606/84 |
| 2011/0087260 A1 | 4/2011 | Seipel et al. | |
| 2011/0306483 A1 | 12/2011 | Valente | |
| 2013/0331876 A1 | 12/2013 | Burroughs, III | |
| 2013/0331877 A1 | 12/2013 | Burroughs, III | |

FOREIGN PATENT DOCUMENTS

WO 2008019097 A2 2/2008

OTHER PUBLICATIONS

International Search Report and Written Opinion for PCT/US2012/036728 mailed Nov. 23, 2012, 10 pages.
International Search Report and Written Opinion for PCT/US2013/044973 mailed Sep. 5, 2013, 12 pages.

(Continued)

*Primary Examiner* — Nicholas Woodall
*Assistant Examiner* — Larry E Waggle, Jr.
(74) *Attorney, Agent, or Firm* — Withrow & Terranova, P.L.L.C.

(57) ABSTRACT

A cutting implement includes a V-shaped blade portion that defines an aperture through which a quadriceps tendon may pass as a doctor harvests the tendon through a minimally invasive procedure.

20 Claims, 11 Drawing Sheets

(56) References Cited

OTHER PUBLICATIONS www.dremed.com/catalog/product_info.php/cPath/45_78/products_id/421, dated May 6, 2011.
www.orsupply.com/medical/category/Cautery+Electrodes/489, dated May 6, 2011.
Non-final Office Action for U.S. Appl. No. 13/493,320 mailed Dec. 23, 2013, 7 pages.
International Preliminary Report on Patentability for PCT/US2012/036728 mailed Nov. 21, 2013, 6 pages.
International Preliminary Report on Patentability for PCT/US13/44973, mailed Jun. 4, 2014, 6 pages.
Final Office Action for U.S. Appl. No. 13/493,320, mailed May 15, 2013, 8 pages.
Non-Final Office Action for U.S. Appl. No. 13/832,638, mailed May 30, 2014, 8 pages.
Advisory Action for U.S. Appl. No. 13/493,320 mailed, Jul. 17, 2014, 3 pages.

* cited by examiner

QUADRICEPS TENDON STRIPPER

FIELD OF THE DISCLOSURE

The present disclosure relates to a cutting instrument adapted to help a surgeon harvest a replacement tendon for an anterior cruciate ligament (ACL) injury from the quadriceps tendon.

BACKGROUND

Figure 1:
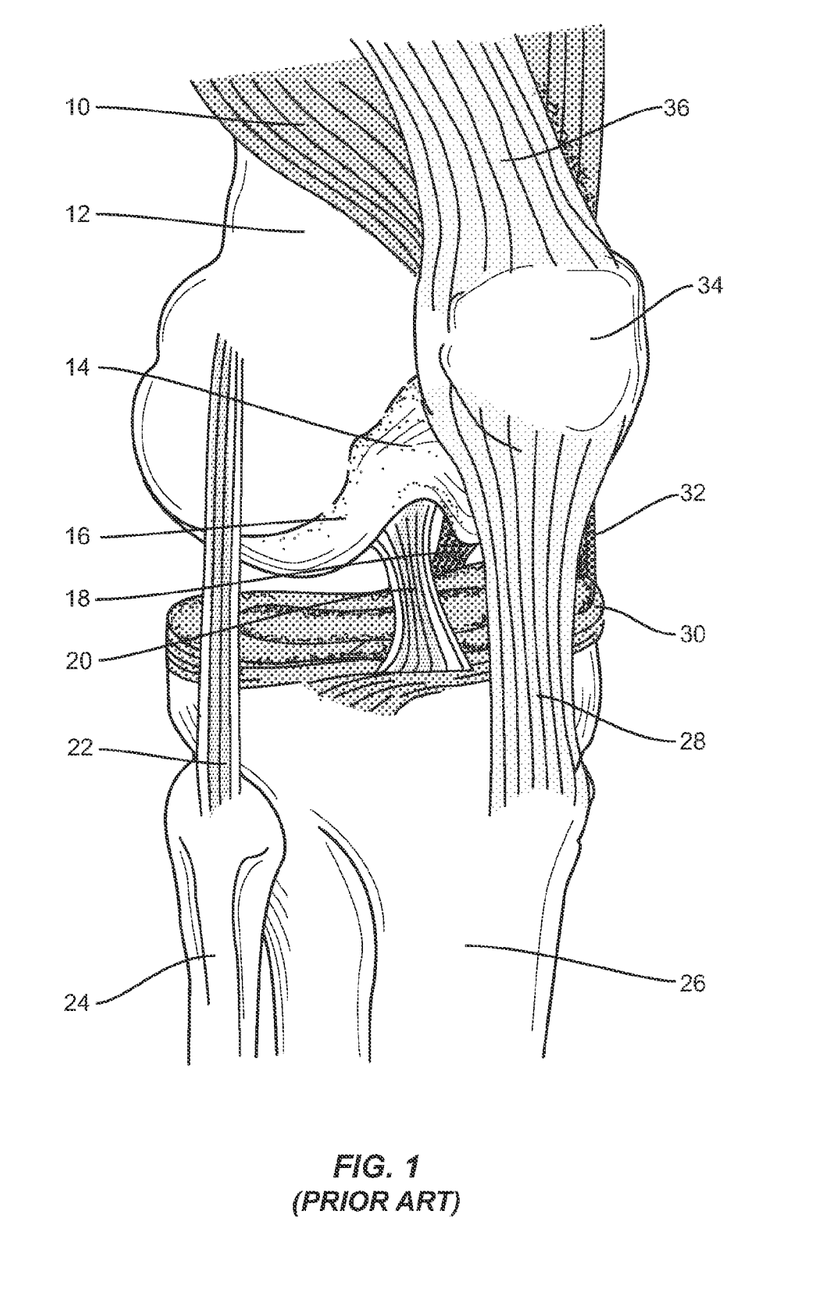
FIG. 1 illustrates a conventional knee.

Most people can go through the majority of their life without ever caring or knowing how complicated a structure the knee that helps them walk is. However, the knee remains a fragile mechanical structure that is readily susceptible to damage. While medical advances have made repairing the knee possible, repair of certain types of injuries results in other long term effects. To assist the reader in appreciating the elegance of the present disclosure, FIG. 1 is provided with a brief explanation of the components of the knee.

For the purposes of the present disclosure, and as illustrated, the knee may be composed of the quadriceps muscles 10, the femur 12, the articular cartilage 14, the lateral condyle 16, the posterior cruciate ligament 18, the anterior cruciate ligament 20, the lateral collateral ligament 22, the fibula 24, the tibia 26, the patellar tendon 28, the meniscus 30, the medial collateral ligament 32, the patella 34 (shown slightly displaced to the side—it normally rests in the center of the knee) and the quadriceps tendon 36. Of particular interest for the purposes of the present disclosure is the anterior cruciate ligament (ACL) 20 and what is done to repair the ACL 20.

ACL tears are common in athletes and are usually season ending injuries. The ACL 20 cannot heal—it must be surgically reconstructed. The reconstruction requires replacement tissue. The most common tissue used is a central slip of the patient's own patellar tendon 28. In practice, the patellar tendon 28 has proven to be generally effective, but the size of the graft that can be used is limited to the size of the patient's own patellar tendon 28. As a rule of thumb, only a third of the patellar tendon 28 may be harvested as a graft. Thus, a doctor will measure the width of the patellar tendon 28, divide by three, and take the middle third of the patellar tendon 28. Such harvested grafts are rarely more than 10 mm wide and may be smaller. Taking this tissue from a person's patellar tendon 28 also causes significant pain and discomfort in the post operative healing period, which may last up to a year, and up to twenty (20) percent of these patients are left with chronic anterior knee pain.

Some doctors recommend and use other graft sources, such as cadaver grafts, but cadaver grafts have a higher failure rate. Additionally, there is a non-zero chance of disease transmission or rejection by the patient's immune system. As a final drawback, cadaver grafts are usually quite expensive and may not be covered by some insurance companies.

Other doctors use hamstring tendons (e.g., the distal semitendinosus tendon) because the scar created during harvesting is relatively small and there is less pain during the rehabilitation, but again, the hamstring tendon has its own collection of disadvantages. The disadvantages include the fact that once the graft is taken, a patient's hamstring will never recover to its previous strength. Further, all hamstring reconstructions stretch and are looser than the original ACL 20. This loosening is particularly problematic in younger female athletes.

Another alternative graft source is the quadriceps tendon 36. The quadriceps tendon 36 is larger and stronger than either the patellar tendon 28 or the hamstring tendon. The quadriceps tendon 36 is likewise stiffer and less prone to stretching or plastic deformation. However, the qualities that make the quadriceps tendon 36 attractive also contribute to the difficulty in harvesting a graft from the quadriceps tendon 36. Existing surgical implements require a large incision up the longitudinal axis of the femur 12 on the front of the thigh to cut down to the level of the tendon 36, resulting in a large post operative scar. Additionally, the quadriceps tendon 36 has a consistency similar to the proverbial shoe leather, making it difficult to cut. However, an ACL 20 repaired with grafts from the quadriceps tendon 36 generally result in almost no anterior knee pain postoperatively over the short or long term and recover quicker. The difficulties in harvesting a quadriceps tendon 36 led to the present disclosure's exploration of an alternate modality for harvesting a graft from the quadriceps tendon 36.

SUMMARY

The present disclosure provides a cutting implement that is adapted to harvest a graft from the quadriceps tendon in a minimally invasive manner. Once the quadriceps tendon graft is secured, it may be used in conventional manners to repair the anterior cruciate ligament (ACL). The cutting implement comprises a handle portion and a blade portion. The blade portion comprises a V-shaped cutting surface that is angled up and away from a distal point of the cutting surface. The space between the arms of the V is open allowing the harvested graft to pass therethrough. A top element spans the distance between the tops of the arms of the V and helps isolate the quadriceps tendon from tissue that is positioned superiorly relative to the tendon.

In alternate embodiments, the top portion may comprise a cutting surface as well or the cutting implement may include a secondary cutting element that is adapted to cut the far end of the quadriceps tendon when a graft of a suitable length has been harvested. In still another embodiment, an auxiliary cutting device may be used to clip the far end of the tendon once the appropriate length has been stripped. The auxiliary cutting device may be a blade, scissors, or an electrocautery device in particularly contemplated embodiments. In another alternate but not mutually exclusive embodiment, the cutting surface of the V-shaped cutting surface is serrated.

In another non-exclusive, alternate embodiment, spacers may be used to adjust the dimension of the cut. The spacers may be a polymeric material and placed between the tendon and the top element, effectively raising the top element away from the tendon, and thus narrowing the width of the V-shape cutting edge that is cutting the tendon.

In another embodiment, a second blade may be used that may fit inside the main blade. The second blade may move independently, reciprocating relative to the main blade so that the two blades operate like a scissor.

Those skilled in the art will appreciate the scope of the disclosure and realize additional aspects thereof after reading the following detailed description in association with the accompanying drawings.

BRIEF DESCRIPTION OF THE DRAWINGS

The accompanying drawings incorporated in and forming a part of this specification illustrate several aspects of the disclosure, and together with the description serve to explain the principles of the disclosure.

DETAILED DESCRIPTION

The embodiments set forth below represent the necessary information to enable those skilled in the art to practice the disclosure and illustrate the best mode of practicing the disclosure. Upon reading the following description in light of the accompanying drawings, those skilled in the art will understand the concepts of the disclosure and will recognize applications of these concepts not particularly addressed herein. It should be understood that these concepts and applications fall within the scope of the disclosure and the accompanying claims.

FIGS. 2-6 illustrate a first exemplary embodiment of a cutting implement 50 according to the present disclosure. The cutting implement 50 includes a handle portion 52 and a blade portion 54. Collectively, the handle portion 52 and blade portion 54 may have a longitudinal length of about ten inches (25.4 cm). The handle portion 52 may include indicia 56 disposed thereon that provide a measurement tool whose use will be explained in greater detail below. The handle portion 52 may be knurled (not shown), have finger indentations (not shown), or have other features to facilitate grasping of the handle portion 52, even during surgery when blood and other bodily fluids might otherwise make the handle portion 52 slippery.

The blade portion 54 includes a first cutting surface 58 and a second cutting surface 60 joined to form a V-shape, with a point 62 and a wide portion 64. The two sides that form the cutting surfaces together define an aperture 66 that extends along the longitudinal axis of the cutting implement 50. The aperture 66 is closed on the top by a top portion 68 that extends across the wide portion 64 of the V-shape. The top portion 68 may include a cutting surface 70 that allows the cutting implement 50 to pass through tissue more readily. Manufacturing constraints may require the point 62 to be a tight curved tip instead of a true point, and as used herein "point" includes both a true point and such curved points.

Figure 3:
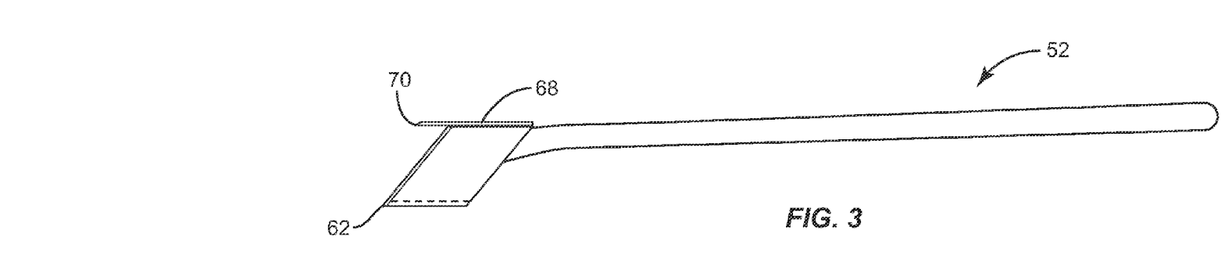
FIG. 3 illustrates a side elevational view of an exemplary embodiment of the cutting implement of the present disclosure.
Figure 4:
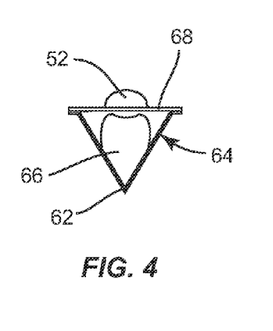
FIG. 4 illustrates a front elevational view of the cutting implement of FIG. 3.
Figure 5:
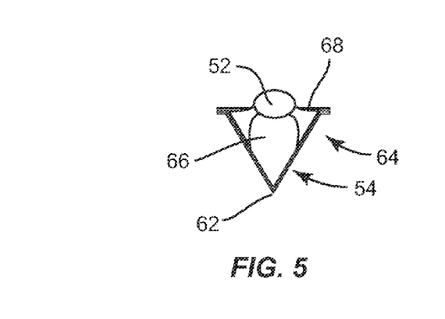
FIG. 5 illustrates a back elevational view of the cutting implement of FIG. 3.
Figure 6:
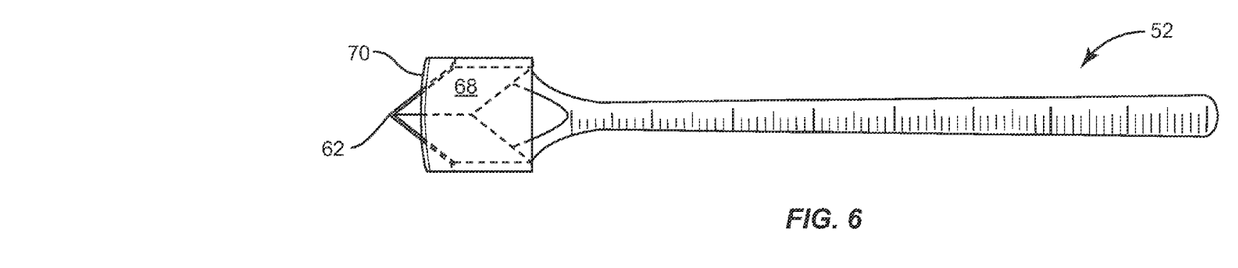
FIG. 6 illustrates a top plan view of the cutting implement of FIG. 3.

As better seen in FIGS. 3 and 6, the top portion 68 extends over at least a portion of the cutting surfaces 58, 60 Likewise, as better seen in FIG. 3, the cutting surfaces 58, 60 slant up and back from the point 62.

Figure 2:
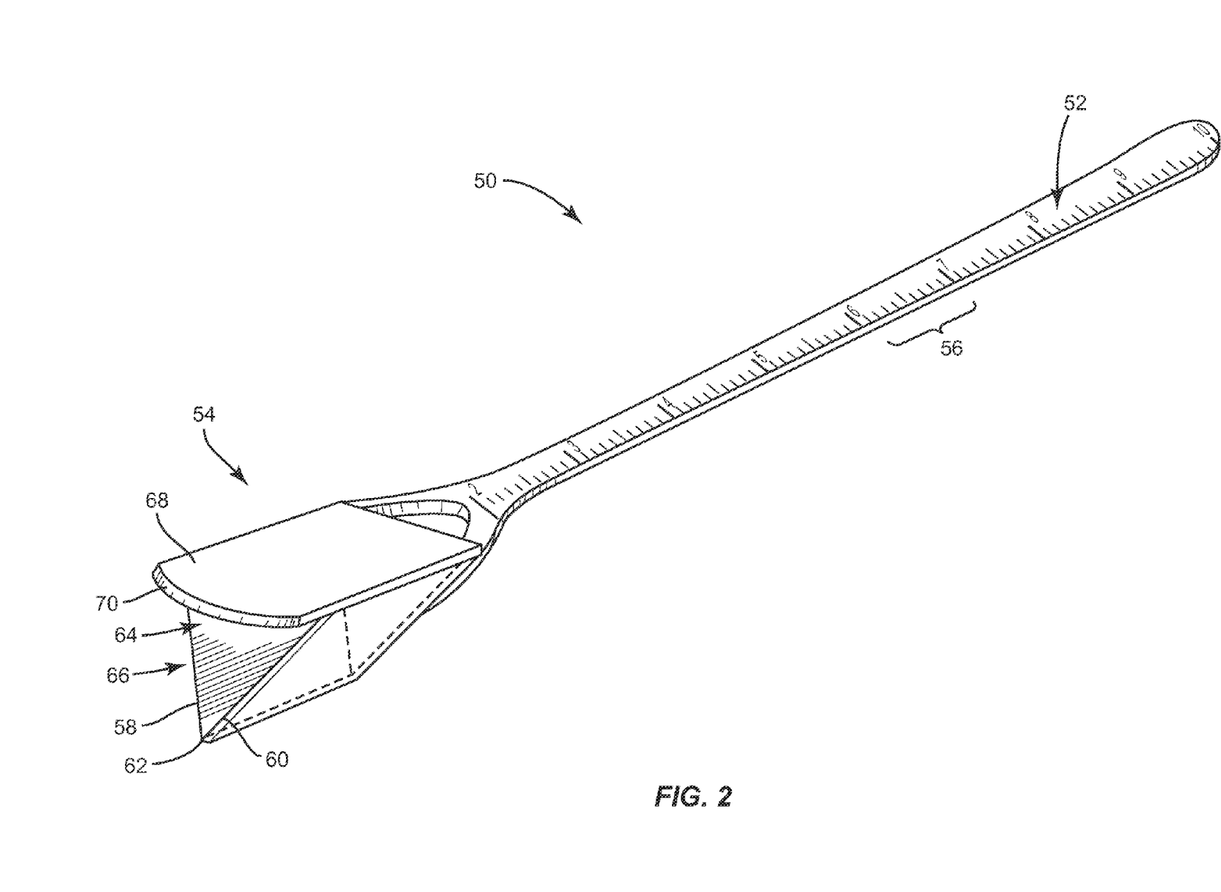
FIG. 2 illustrates a perspective view of an exemplary embodiment of the cutting implement of the present disclosure.

In an exemplary embodiment, at least the blade portion 54 is made of surgical grade steel and the cutting surfaces 58, 60 are honed to a high degree of sharpness comparable to that of a conventional scalpel. Alternatively, the cutting surfaces 58, 60 could be a synthetic diamond scalpel blade having a cutting width of approximately 3 nm or some form of cracked glass (e.g., obsidian), which may have cutting edges on the order of 200 Angstroms. Exemplary diamond scalpels are sold by Clinicon Corporation of Oceanside Calif. Exemplary obsidian scalpels are sold by Fine Science Tools of Foster City Calif.

Figure 15:
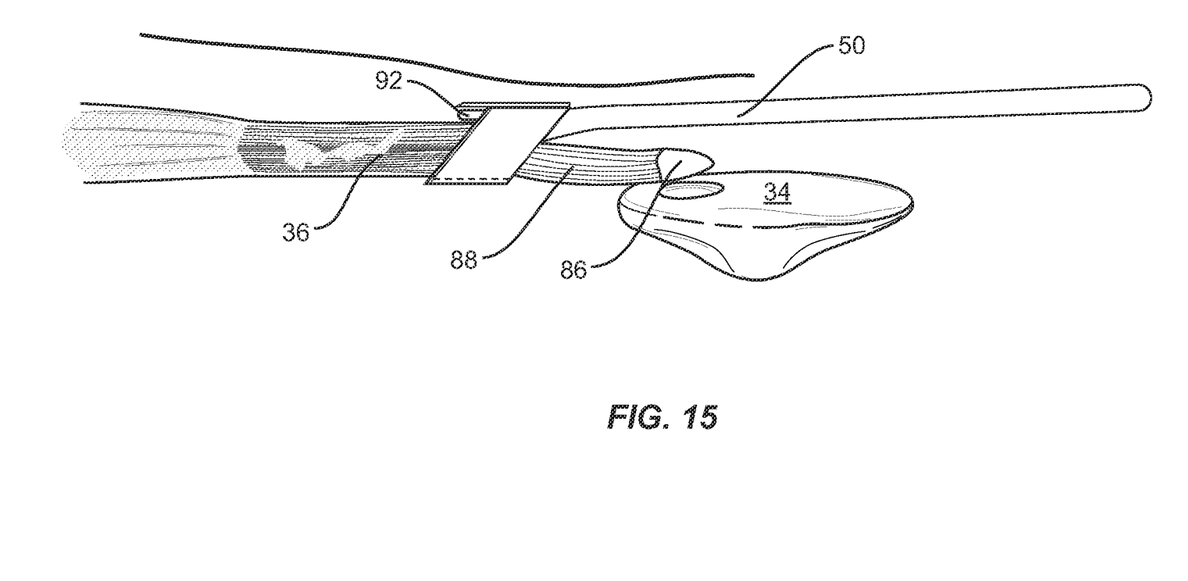
FIG. 15 illustrates spacers that may be used to control the width of the cut.

The cutting implement 50 may be part of a kit that includes the cutting implement 50, a cutting guide 72 (FIGS. 7-9), and a spacer 74 (FIG. 15). Additionally, the kit may include an auxiliary cutting element such a pair of scissors or an electrocautery cutting element as described in greater detail below. This kit may be made as a single use kit, or the elements of the kit may support multiple sterilizations in an autoclave or comparable sterilization environment.

Figure 7:
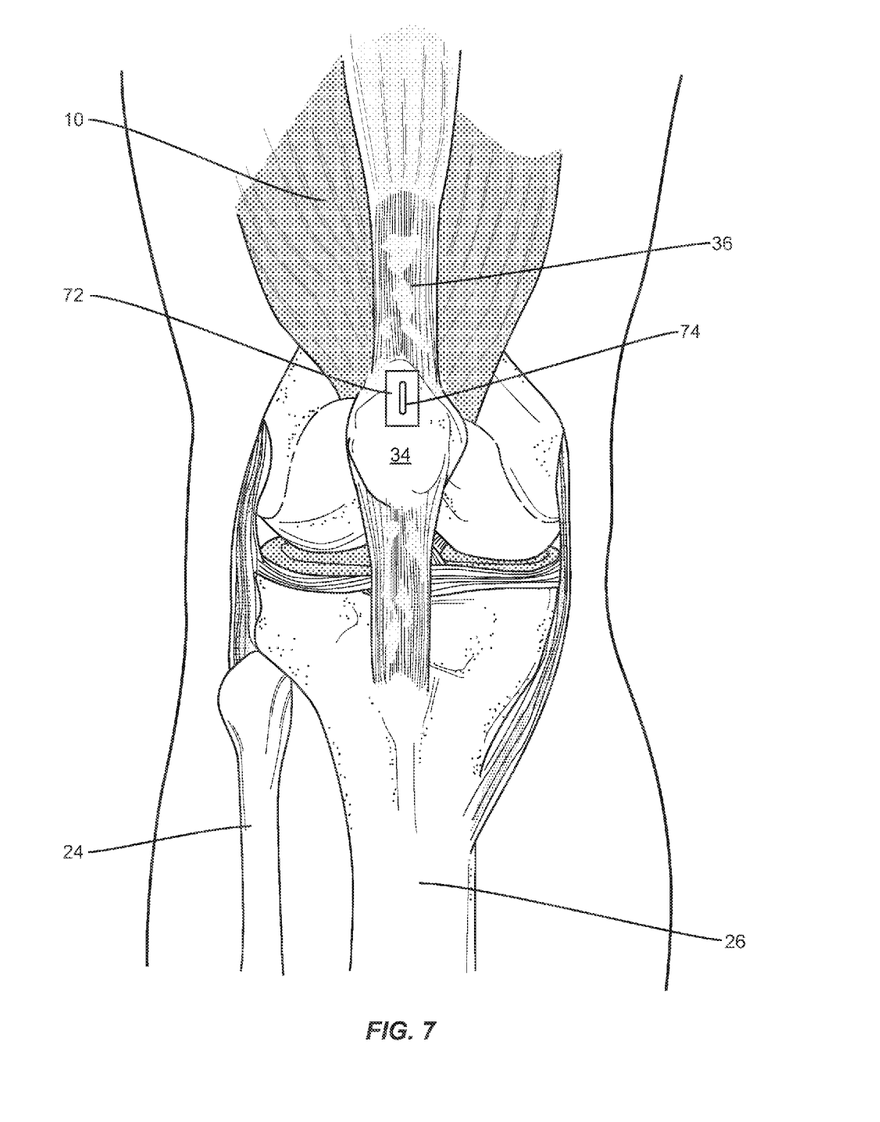
FIG. 7 illustrates a knee with a bone graft guide positioned thereon as is done at the beginning of tendon harvesting.
Figure 8:
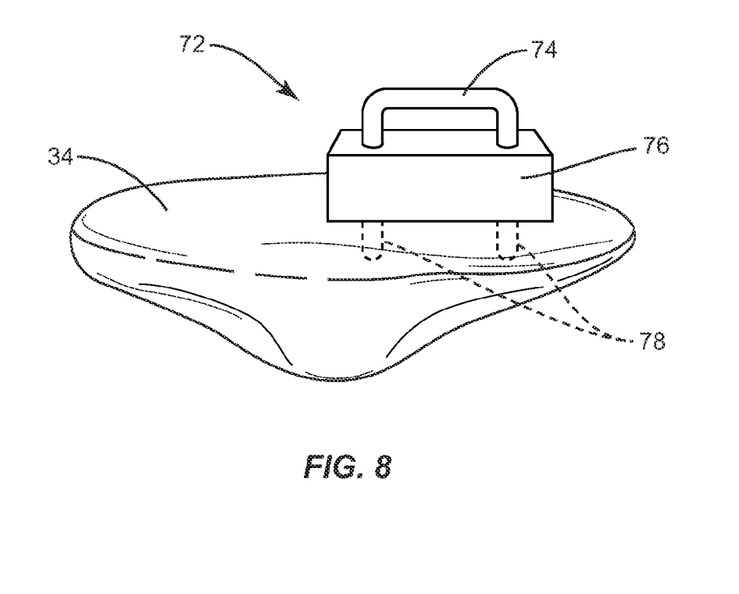
FIGS. 8 and 9 illustrate the bone graft guide positioned on the patella as is used to form the bone graft.
Figure 9:
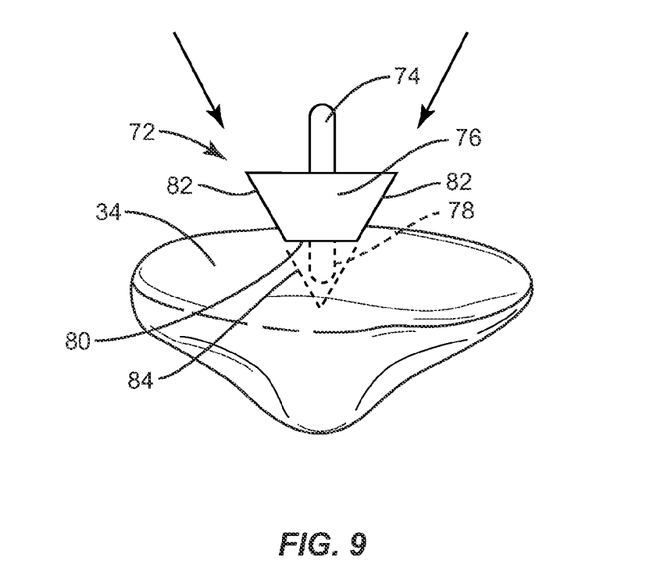
Figure 11:
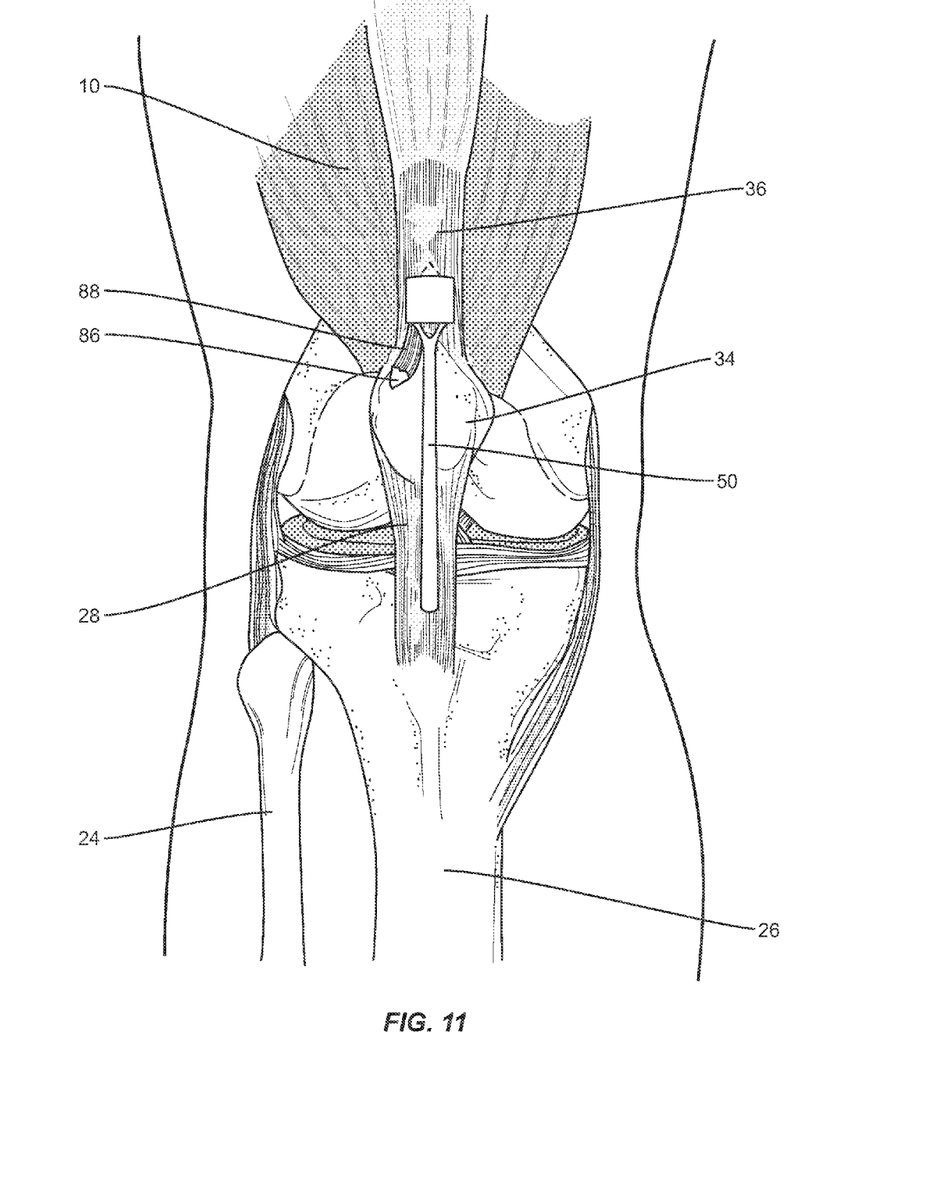
FIG. 11 illustrates the cutting implement with a portion of the harvested graft extending from the back end of the cutting implement.

The cutting guide 72 is illustrated in use in FIGS. 7-9. The cutting guide may be generally trapezoidally shaped body 76 (FIG. 9) and includes an optional handle 74 and posts 78. The bottom surface 80 of the body 76 may be about eleven (11) mm across, although other dimensions are also possible. In an exemplary embodiment, the width of the bottom surface is slightly smaller than the width of the wide portion 64 of the blade portion 54 of the cutting implement 50. Furthermore, the sidewalls 82 are slanted such that if the sidewalls 82 were extended past the bottom surface 80, an equilateral triangle 84 is formed. In use, a chisel or other cutting implement is placed next to the guide 72 and used to cut into the patella 34. The cuts made in this fashion cut an equilateral triangle bone plug 86 (FIG. 11) that fits within the aperture 66 of the cutting implement 50.

Figure 10:
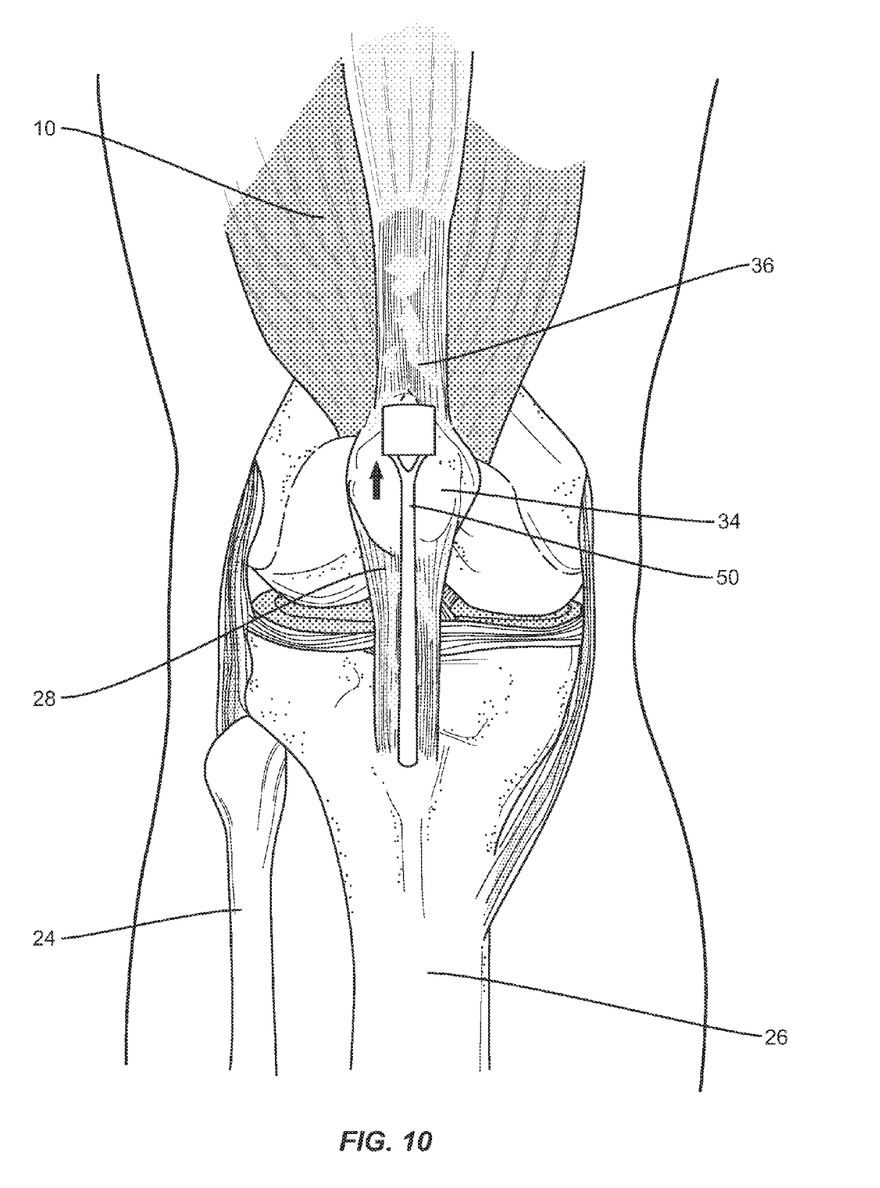
FIG. 10 illustrates the cutting implement beginning to cut the quadriceps tendon.

Once the bone plug 86 has been cut, the guide 72 is removed, and surgical thread is threaded into the holes for the posts 78, the thread is then pulled up, effectively fishing the bone plug 86 out of the patella 34. When selecting the place from which to create the bone plug 86, at least a portion of the bone plug 86 should be attached to the quadriceps tendon 36. Thus, when the bone plug 86 is extracted from the patella 34, it is still attached to the quadriceps tendon 36. The bone plug 86 is then fed into the aperture 66 and the cutting implement is ready to begin cutting (see FIG. 10). The cutting implement 50 is then pushed anteriorly up the longitudinal axis of the femur 12, beneath the skin of the patient. The sharp cutting surfaces 58, 60 cut through the tough quadriceps tendon 36. The doctor may compare the length of harvested tendon 88 (FIG. 11) to the indicia 56 to see if the doctor has harvested or stripped enough tendon 36.

Figure 12:
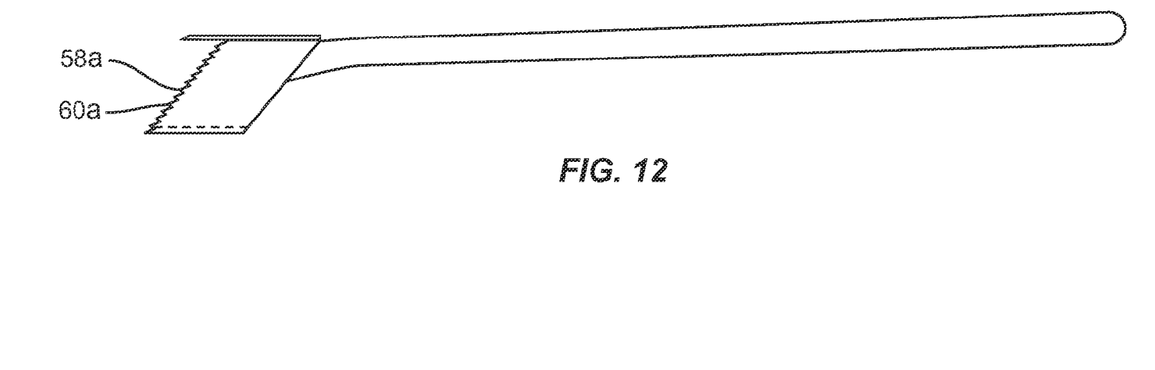
FIG. 12 illustrates an alternate embodiment with a serrated blade.

FIG. 12 illustrates an alternate embodiment wherein the cutting surfaces 58a, 60a are serrated. In some situations, the serrations may make it easier to cut the tough tendon 36.

Figure 13:
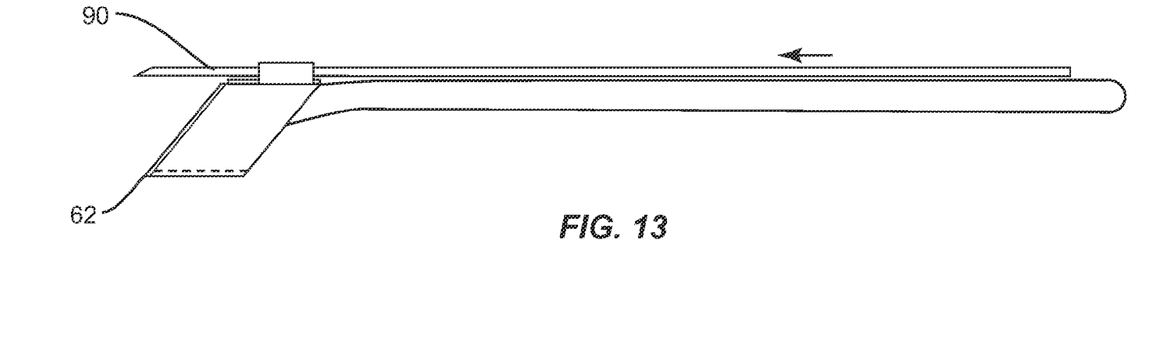
FIG. 13 illustrates another alternate embodiment with a distinct and selectively extendable distal cutting element.

FIG. 13 illustrates another alternate embodiment, wherein a selectively extendable blade 90 is positioned on the top surface 68. The extendable blade 90 may be used to sever the far end of the tendon 36 once an acceptable length of tendon has been harvested. In a first, retracted position the blade 90 may be positioned within a sheath. In a second, extended position, the blade 90 may be exposed and extend past the front of the top surface 68 such that the blade is approximately as far forward as the distal point 62.

FIG. 15 illustrates a spacer 92, which in an exemplary embodiment comprises a polymeric washer shape approximately 1 mm thick. The spacer 92 may be positioned underneath the top surface 68 on the tendon 36. Because the aperture 66 is an equilateral triangle, each spacer 92 effectively lifts the cutting surfaces 58, 60 an equal distance and effectively narrows the amount of tendon 36 that is harvested. For example, if the wide portion 64 is eleven mm wide, one spacer 92 would lift the blades one mm, causing the widest cutting part to now be ten mm. Additional spacers 92 may be stacked to reduce the width of the harvesting further as needed.

Figure 16A:
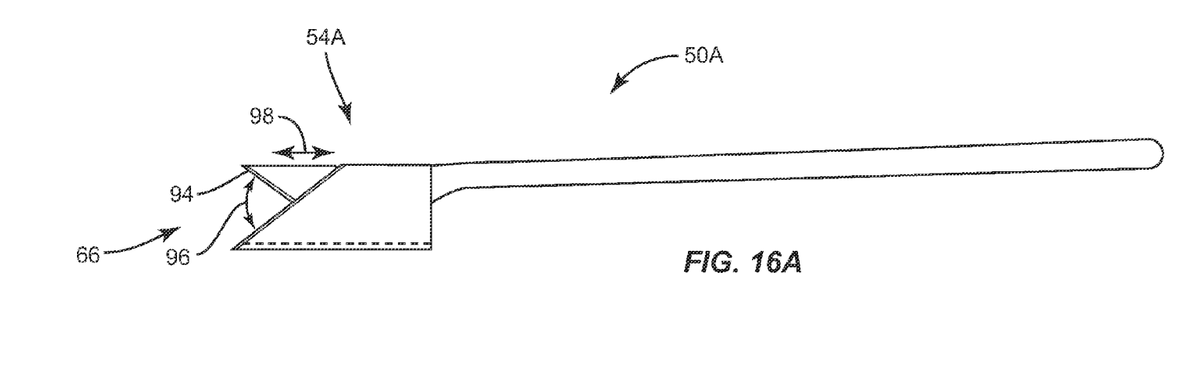
FIGS. 16A and 16B illustrate an embodiment with a scissor type cutting element.
Figure 16B:
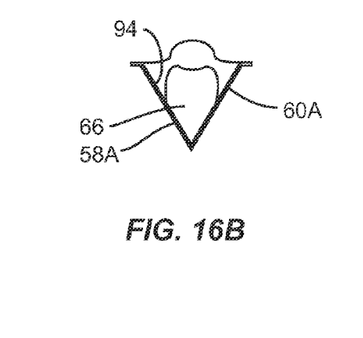

FIGS. 16A and 16B illustrate another alternate embodiment wherein the cutting implement 50A has a scissor-like cutting portion 54A. As illustrated, the cutting portion 54a includes primary cutting surfaces 58A, 60A and reciprocating V-shaped cutting surface 94 that moves relative to the primary cutting surfaces 58A, 60A. In a first embodiment, the cutting surface 94 moves up and down in a generally arcuate motion (generally indicated at 96), and the cutting effect is achieved as the blades close, similar to conventional scissors. In a second embodiment, the cutting surface 94 moves along the longitudinal axis of the cutting implement 50A (generally indicated at 98) so that the cutting surface 94 moves in and out of the aperture 66.

Figure 17:
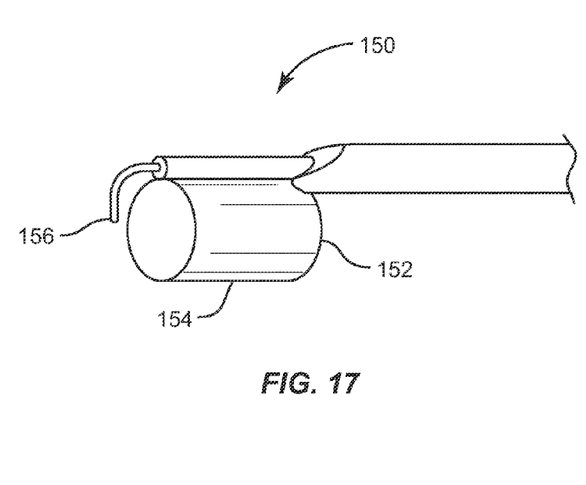
FIG. 17 illustrates an electrocautery tip auxiliary cutting element.

FIG. 17 illustrates an auxiliary cutting element 150 that is used to sever the distal end of the quadriceps tendon 36. The auxiliary cutting element 150 may be an electrocautery element shaped like a cylinder 152 with a short axis 154 and an insulated, rotating cautery tip 156 selectively extendable at a distal end of the element 150. In practice, the cutting element 50 is used to strip a section of the tendon 36. Then the cutting element 50 is withdrawn, and the bone plug 86 and the harvested tendon 88 are fed through the cylinder 152 of the auxiliary cutting element 150. The cautery tip 156 is then simultaneously extended, rotated, and heated (or heated and extended and rotated). The cautery tip 156 rotates inwardly towards the center of the cylinder 152. The auxiliary cutting element 150 is rotated about the harvested tendon 88, moving the extended cautery tip 156 through the distal end of the harvested tendon 88. This movement effectively cuts the tendon 88 at the far point and is believed to be less invasive than simply advancing the cutting implement 50 to the end of the tendon 36 and into the muscle (which would effectively "tear" the harvested tendon 88 from the attached fibers and the quadriceps). Cautery elements are known and can be adapted from those sold by websites such as www.dremed.com/catalog/product_info.php/cPath/45_78/products_id/421 and www.orsupply.com/medical/category/Cautery+Electrodes/489.

In another embodiment, not specifically illustrated, a cutting implement could take the form of a pair of scissors such as a modified pair of OB-GYN scissors. In particular, the scissors may be modified so that the hinge is more in the middle of the scissor than is typical. By moving the hinge, the scissors can be used deep in the wound, keeping the incision small. Still other cutting implements could be used to sever the distal end of the harvested tendon 88 as desired.

Figure 14:
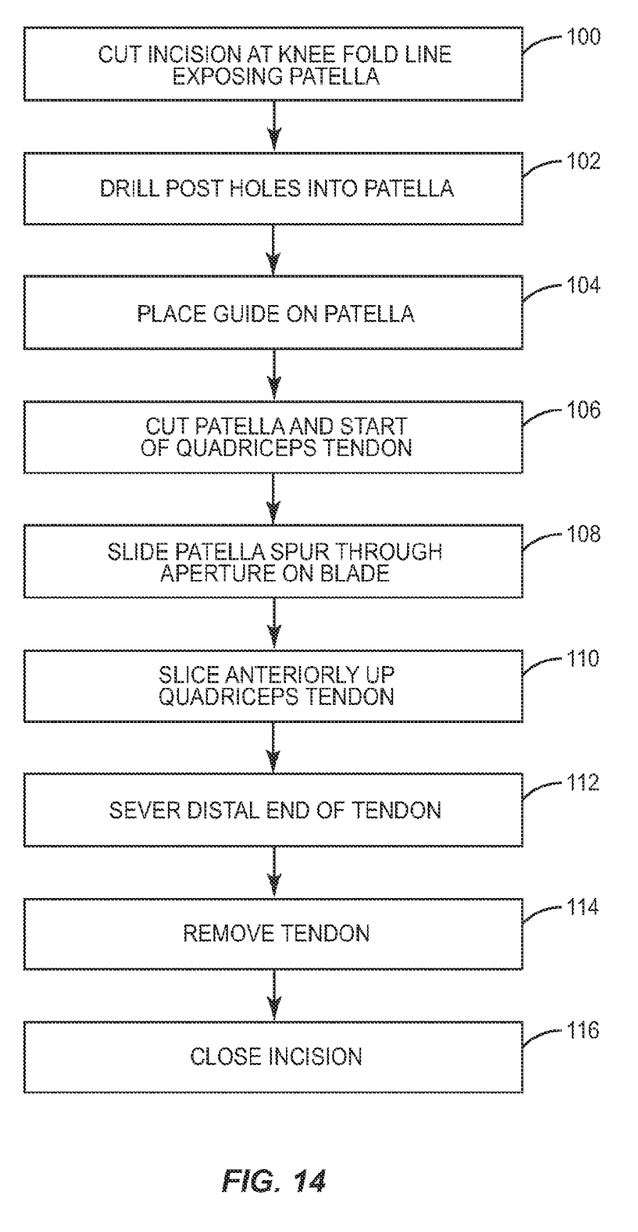
FIG. 14 illustrates a flow chart setting forth the method of using the cutting implement of the present disclosure.

FIG. 14 illustrates a flow chart explaining use of the cutting implement 50. The doctor makes an initial incision at a knee fold line (block 100), such as an anterior fold line, and folds the skin back to expose a portion of the patella 34. The doctor drills two post holes into the patella 34 proximate the quadriceps tendon 36 (block 102). The holes may be approximately eleven mm deep in an exemplary embodiment. The doctor then places the guide 74 on the patella 34, with the posts 78 positioned within the holes (block 104). The doctor will chose the width of the quadriceps tendon to be harvested by measuring the size of the quadriceps tendon preoperatively from MRI imaging and comparing them to the intraoperative observations of the tendon itself. Cross sectional area of the patellar tendon can be calculated from the MRI, and one third this patellar tendon area can be compared to the cross sectional areas resulting from different quadriceps options based on the areas of the equilateral triangles resulting.

Next the bone plug 86 is created by cutting into the patella 34 using the sidewalls of the guide 74 to guide the cuts into the patella 34, thereby creating the equilateral bone plug 86 and the initial cut into the quadriceps tendon 36 (block 106). The guide 74 directs the saw blade such that the resulting bone plug 86 is of the same dimensions as the quadriceps graft that has been chosen, allowing it to be slipped through the aperture 66 on the blade portion 54 (block 108). The graft may be secured by sutures based through the original holes drilled at the beginning of the procedure, facilitating passage of the bone plug 86. If necessary, the doctor inserts one or more spacers 92 to space the top surface 68 from the tendon 36, narrowing the cutting width. The doctor then slices anteriorly up the quadriceps tendon 36 underneath the skin of the patient (block 110). When an appropriate length of tendon 36 has been cut, the doctor severs the distal end of the tendon 36, (block 112), such as by rotating the top portion 68 into contact with the tendon 36 and sawing, or selectively extending the extendable blade 90 and using it to saw through the tendon 36. Alternatively, a second blade may be inserted through the incision and used to cut the distal end of the tendon 36. As still another option, the doctor may insert the auxiliary cutting implement 150, extend the cautery tip 156 and cauterize the end of the tendon 36. Still another option is to make a new incision further up the thigh proximate the distal end and make a cut into the tendon 36 at the second incision. The doctor then removes the tendon (block 114) and closes the incision (block 116).

Those skilled in the art will recognize improvements and modifications to the embodiments of the present disclosure. All such improvements and modifications are considered within the scope of the concepts disclosed herein and the claims that follow.

What is claimed is:

1. A surgical instrument comprising:
    a handle portion; and
    a blade portion joined to the handle portion, the blade portion comprising:
        a first cutting surface;
        a second cutting surface joined to the first cutting surface to form a V-shape having a point and a wide portion, such that the cutting surfaces slant up and back from the point, the first and second cutting surfaces defining an aperture extending through the blade portion; and
        a top portion extending across the wide portion of the V-shape, the top portion having a handle side proximate the handle portion, the top portion having a front edge opposite the handle side, and the point of the blade portion extending away from the handle portion past the front edge of the top portion; and
    a spacer selectively positionable beneath the top portion to space the top portion from a work piece being cut by the first and second cutting surfaces.

2. The surgical instrument of claim 1 wherein the blade portion comprises a steel blade portion.

3. The surgical instrument of claim 1 wherein the first and second cutting surfaces comprise serrated cutting surfaces.

4. The surgical instrument of claim 1 further comprising a third cutting surface movably positioned on the top portion such that in a first position the third cutting surface extends past the front edge of the top portion and is available to cut and in a second position the third cutting surface is retracted and not available to cut.

5. The surgical instrument of claim 1 wherein the first and second cutting surfaces are adapted to cut a quadriceps tendon and in so doing, pass a cut portion of the quadriceps tendon through the aperture.

6. The surgical instrument of claim 1 wherein the top portion does not include a cutting surface.

7. The surgical instrument of claim 1 further comprising a second cutting element positioned within the blade portion and adapted to reciprocate along a longitudinal axis of the surgical instrument.

8. The surgical instrument of claim 1 wherein the aperture through the blade portion is configured such that a workpiece may pass through the blade portion and out underneath the handle portion.

9. A surgical kit comprising:
   a spacer;
   a guide adapted to assist a surgeon in creating a bone plug extract from a patella; and
   a cutting instrument comprising:
      a handle portion; and
      a blade portion joined to the handle portion, the blade portion comprising:
         a first cutting surface;
         a second cutting surface joined to the first cutting surface to form a V-shape having a point and a wide portion, such that the cutting surfaces slant up and back from the point, the first and second cutting surfaces defining an aperture extending through the blade portion; and
         a top portion extending across the wide portion of the V-shape, the top portion having a handle side proximate the handle portion, the top portion having a front edge opposite the handle side, and the point of the blade portion extending away from the handle portion past the front edge of the top portion; and
   wherein the spacer is selectively positionable beneath the top portion to space the top portion from a work piece being cut by the first and second cutting surfaces.

10. The surgical kit of claim 9 wherein the first and second cutting surfaces are serrated.

11. The surgical kit of claim 9 wherein the spacer is adapted to fit underneath the top portion and space the top portion from a quadriceps tendon while the cutting surfaces are cutting the quadriceps tendon.

12. The surgical kit of claim 9 wherein the guide comprises at least one post adapted to be positioned within a hole in the patella.

13. The surgical kit of claim 9 wherein the spacer comprises a polymeric material.

14. A surgical instrument comprising:
   a handle portion;
   a blade portion joined to the handle portion, the blade portion comprising:
      a first cutting surface;
      a second cutting surface joined to the first cutting surface to form a V-shape having a point and a wide portion, such that the cutting surfaces slant up and back from the point, the first and second cutting surfaces defining an aperture extending through the blade portion; and
      a top portion extending across the wide portion of the V-shape; and
   a second cutting element positioned within the blade portion and adapted to reciprocate along a longitudinal axis of the surgical instrument.

15. The surgical instrument of claim 14 wherein the blade portion comprises a steel blade portion.

16. The surgical instrument of claim 14 wherein the first and second cutting surfaces comprise serrated cutting surfaces.

17. The surgical instrument of claim 14 wherein the first and second cutting surfaces are adapted to cut a quadriceps tendon and in so doing, pass a cut portion of the quadriceps tendon through the aperture.

18. The surgical instrument of claim 14 wherein the top portion does not include a cutting surface.

19. A surgical instrument comprising:
   a handle portion; and
   a blade portion joined to the handle portion, the blade portion comprising:
      a first cutting surface;
      a second cutting surface joined to the first cutting surface to form a V-shape having a point and a wide portion, such that the cutting surfaces slant up and back from the point, the first and second cutting surfaces defining an aperture extending through the blade portion; and
      a top portion extending across the wide portion of the V-shape; and
      a third cutting surface movably positioned on the top portion, such that in a first position the third cutting surface extends past the front edge of the top portion and is available to cut and in a second position the third cutting surface is retracted and not available to cut.

20. The surgical instrument of claim 19 wherein the blade portion comprises a steel blade portion.

* * * * *